United States Patent [19]  [11] 4,440,875
Kortbeek et al.  [45] Apr. 3, 1984

[54] CATALYTIC PROCESS FOR THE PRODUCTION OF HYDROCARBONS FROM SYNGAS

[75] Inventors: Andras G. T. G. Kortbeek; Guy Barré; Jean M. Durel, all of Grand Couronne, France

[73] Assignee: Shell Oil Company, Houston, Tex.

[21] Appl. No.: 408,382

[22] Filed: Aug. 16, 1982

[30] Foreign Application Priority Data

Sep. 28, 1981 [FR] France .................. 81 18208

[51] Int. Cl.³ .............................................. C07C 1/04
[52] U.S. Cl. ...................................... 518/728; 502/344
[58] Field of Search ........................................ 518/728

[56] References Cited

U.S. PATENT DOCUMENTS 3,702,886 11/1972 Argauer et al. ............... 252/455 Z
4,177,202 12/1979 Chang et al. ........................ 518/714

FOREIGN PATENT DOCUMENTS 1489357 10/1977 United Kingdom ............... 518/728

Primary Examiner—Howard T. Mars
Attorney, Agent, or Firm—John M. Duncan

[57] ABSTRACT

Process for the production of hydrocarbons from synthesis gas in which the gas is passed at elevated pressure and temperature over a catalyst consisting of zirconium oxide promoted with at least one alkali metal compound. Preferably the zirconium oxide has a specific surface area in the range from 20 to 500 m²/g and the alkali metal compound is potassium oxide. A major part of the product consists of butene.

7 Claims, No Drawings

CATALYTIC PROCESS FOR THE PRODUCTION OF HYDROCARBONS FROM SYNGAS

BACKGROUND OF THE INVENTION

The invention relates to a process for the production of hydrocarbons from synthesis gas, characterized in that the synthesis gas is passed at elevated pressure and temperature over a catalyst consisting of zirconium oxide promoted with at least one alkali metal compound. The catalyst may be supported on a suitable carrier such as alumina or silica.

A process for converting synthesis gas to hydrocarbons over unpromoted zirconium oxide is described in an article by H. H. Storch et al in "The Fischer Tropsch and Related Synthesis" at pages 455–463 (John Wiley & Sons, New York) which is incorporated herein by reference.

SUMMARY OF THE INVENTION

A process is provided for the production of hydrocarbons from synthesis gas, wherein the synthesis gas is passed at conversion conditions of elevated pressure and temperature over a catalyst consisting of zirconium oxide promoted with at least one alkali metal compound.

DETAILED DESCRIPTION

In the process according to the invention the starting material is synthesis gas, i.e., a gaseous mixture consisting subtantially of $H_2$ and CO. Such $H_2/CO$ mixtures can very suitably be prepared by steam gasification or partial combustion of a carbon-containing material. Examples of such materials are wood, peat, brown coal, bituminous coal, anthracite, coke, crude mineral oil and fractions thereof as well as tars and oils extracted from tar sand and bituminous shale. The steam gasification of partial combustion is preferably carried out at a temperature of 900°–1600° C. and a pressure of 10–100 bar. In the process according to the invention it is advantageous to start from an $H_2/CO$ mixture with an $H_2/CO$ molar ratio of more than 0.25 and less than 6.

The intention is to convert the largest possible quantity of the CO present in the feed into hydrocarbons. To this end the $H_2/CO$ molar ratio in the feed is suitably about 1.0.

The process according to the invention can very suitably be carried out by conducting the feed in upward or downward direction through a vertically mounted reactor containing a fixed bed of the catalyst or by passing the gaseous feeds upwardly through a fluid catalyst bed. The process can also be carried out using a suspension of the catalyst or catalyst combination in a hydrocarbon oil. The process is preferably carried out under the following conditions: a temperature in the range from 200° to 600° C. and in particular from 300° to 500° C., a pressure in the range from 0.1 to 1000 bar and in particular from 5 to 200 bar and a space velocity in the range from 100 to 5000 Nl synthesis gas/l catalyst/hour.

In order to improve the hydrocarbon yield of the process according to the invention a catalyst is applied having an extensive specific surface area, preferably in the range from 20 to 500 $m^2/g$. Such a $ZrO_2$ catalyst is prepared in the following way: zirconiumoxychloride ($ZrOCl_2$) is dissolved in water. While stirring, ammonia is gradually added to the solution until the pH of the solution is in the range from 7 to 10. The precipitated zirconium hydroxide is separated from the solution by filtration and washed. It is then calcined from 1 to 24 hours in air at a temperature in the range from 300° to 1000° C.

By adding an alkali metal compound to the catalyst the selectivity for $C_4$-hydrocarbons and especially the selectivity for butene is improved. Therefore, the process is carried out using a catalyst promoted with an alkali metal compound, such as an alkali metal hydroxide, nitrate or carbonate.

In order to improve the activity and stability of the catalyst it is advantageously calcined before being used, suitably at a temperature in the range from 400° to 800° C.

Although any alkali metal compound may be used as catalyst promoter in the present process, preference is given to a potassium compound because it is readily available, cheap and it gives good results as to selectivity improvement.

The alkali metal content of the catalyst is advantageously chosen between 0.5 and 50% by weight, and preferably between 0.4 and 10% by weight.

The invention will now be elucidated by means of the following Example.

EXAMPLE

A gaseous mixture of hydrogen and carbon monoxide having a $CO/H_2$ molar ratio of 1 was passed over a bed of zirconium oxide catalyst particles containing 1% by weight of potassium in the form of $K_2O$ and having a specific surface area of 122 $m^2/g$ which was the result of a previous calcination step carried out in air for 2 hours at 450° C. The catalyst particles size was from 0.4–0.6 mm.

The reaction conditions were chosen as follows:
Temperature: 450° C.
Pressure: 20 bar abs.
Gas hourly space velocity: 1000 Nl/l.h
The CO-conversion to hydrocarbons was 11%.
The hydrocarbon product had the following composition:

| | Hydrocarbons % wt | Paraffins % wt | Olefins % wt |
|---|---|---|---|
| $C_1$ | 30 | — | — |
| $C_2$ | 13 | 5 | 8 |
| $C_3$ | 5 | — | 5 |
| $C_4$ | 52 | 12 | 40 |
| $C_5$ | — | — | — |

The $C_3$-product consisted of 100% propene.
The molar ratio between butene and butane in the product was 3.5.

COMPARATIVE EXPERIMENT 1

The experiment of the Example was repeated using the same conditions with the exception that the catalyst did not contain potassium.
The CO-conversion was 30%.
The hydrocarbon product composition was:

| | Hydrocarbons % wt | Paraffins % wt | Olefins % wt |
|---|---|---|---|
| $C_1$ | 21 | 21 | — |
| $C_2$ | 9 | 6 | 3 |
| $C_3$ | 4 | 1 | 3 |
| $C_4$ | 55 | 24 | 31 |

| | Hydrocarbons % wt | Paraffins % wt | Olefins % wt |
|---|---|---|---|
| $C_5$ | 11 | 4 | 7 |

The propene/propane molar ratio and the butene/butane molar ratio in the product were 2.18 and 0.87, respectively.

By comparing the results given in the Example with those of the comparative experiment it can be concluded that by adding an alkali metal compound to the catalyst the olefin content of the product is increased and especially the selectivity to butene is markedly improved.

COMPARATIVE EXPERIMENT 2

A gaseous mixture of hydrogen and carbon monoxide having a $CO/H_2$ molar ratio of 1 was passed over a bed of titanium oxide as catalyst having a specific surface area of 121 m²/g which had been calcined in air for 2 hours at 400° C. The catalyst particles size was from 0.4–0.6 mm.

The reaction conditions were the same as those used in the Example.

The CO-conversion to hydrocarbons was 13%.

The hydrocarbon product had the following composition:

| | Hydrocarbons % wt | Paraffins % wt | Olefins % wt |
|---|---|---|---|
| $C_1$ | 70.7 | 70.7 | — |
| $C_2$ | 12.5 | 11.6 | 0.9 |
| $C_3$ | 4.0 | 2.3 | 1.7 |
| $C_4$ | 10.3 | 5.4 | 4.9 |
| $C_5$ | 2.6 | 2.6 | — |

The ethylene/ethane, propene/propane and butene/butane molar ratios in the product were 0.08, 0.80 and 0.94, respectively.

By comparing the results given in the Example with those of this comparative experiment it can be concluded that zirconium oxide shows unique properties with respect to the selective production of $C_4$-hydrocarbons, in particular $C_4$-olefins.

What is claimed is:

1. A process for the selective production of $C_4$ hydrocarbons from synthesis gas, wherein the synthesis gas is passed at conversion conditions of elevated pressure and temperature over a catalyst consisting of zirconium oxide promoted with at least one alkali metal compound.

2. The process of claim 1, wherein the zirconium oxide has a specific surface area in the range from 20 to 500 m²/g.

3. The process of claim 2, wherein the alkali metal compound is alkali metal oxide.

4. The process of claim 3, wherein the alkali metal compound is $K_2O$.

5. The process of claim 3, wherein the catalyst contains an alkali metal content in the range from 0.05 to 50% by weight.

6. The process of claims 1 or 5, wherein the process is carried out at a pressure in the range from 0.1 to 1000 bar abs., a temperature in the range from 200° to 600° C. and a space velocity in the range from 100 to 5000 normal liters synthesis gas per liter of catalyst per hour.

7. The process of claim 6, wherein the synthesis gas consists substantially of $H_2$ and CO, the $H_2/CO$ molar ratio being in the range from 0.25 to 6.0.

* * * * *